United States Patent [19]

Langdon

[11] Patent Number: 5,217,023
[45] Date of Patent: Jun. 8, 1993

[54] CYTOLOGY COLLECTION DEVICE AND METHOD

[75] Inventor: Robert S. Langdon, Bedford, N.H.

[73] Assignee: Langdon Medical, Inc., Bedford, N.H.

[21] Appl. No.: 679,623

[22] Filed: Apr. 3, 1991

[51] Int. Cl.[5] .................................................. A61B 10/00
[52] U.S. Cl. ................................................................ 128/756
[58] Field of Search .............................. 128/749-756; 606/167, 170, 171

[56] References Cited

U.S. PATENT DOCUMENTS

| | | | |
|---|---|---|---|
| 2,839,049 | 6/1958 | MacLean . | |
| 3,074,396 | 1/1963 | MacLean . | |
| 3,945,371 | 3/1976 | Adelman . | |
| 4,235,244 | 11/1980 | Abele et al. | 128/749 |
| 4,235,245 | 11/1980 | Naito | 128/756 |
| 4,245,653 | 1/1981 | Weaver | 128/750 |
| 4,361,948 | 12/1982 | Omata | 128/756 |
| 4,494,555 | 1/1985 | Abrioux et al. | 128/755 |
| 4,512,344 | 4/1985 | Barber | 128/755 |
| 4,646,738 | 3/1987 | Trott | 128/752 |
| 4,763,667 | 8/1988 | Manzo | 128/750 |
| 4,936,312 | 6/1990 | Tsukagoshi | 128/749 |
| 4,966,162 | 10/1990 | Wang | 128/756 |
| 5,056,529 | 10/1991 | de Groot | 128/756 |

OTHER PUBLICATIONS

*Medi-Tech Contamination Free Microbiology Specimen Brush*, BFW/1.0/70/90, Meditech Division, Cooper Scientific Corporation Oct. 1978.

*The New Mill-Rose Disposable Cytology Brush*, Mill-Rose Laboratories, Inc. Feb. 23, 1977.

*A New Rapid Method for Stomach-Cancer Diagnosis: The Gastric Brush*, "Cancer" vol. 6, No. 6, Nov. 1953, pp. 1177-1180.

*Use of a New Controllable-Tip Brush With the Flexible Fiber Bronchoscope*, reprinted from Chest, vol. 66, pp. 620-621, Jun. 1974.

Primary Examiner—Max Hindenburg
Attorney, Agent, or Firm—Davis, Bujold & Streck

[57] ABSTRACT

A cytology collection device in which a debriding brush 3 is supported by a flexible elongate support 1 extending through a flexible tube 6 through which a specimen to be collected may be sucked. The brush is arranged for rotation by the support and is retractable within the tube during process of inserting the device through a scope 10 in preparation for the collection of a specimen. Once the site to be investigated has been reached, the brush is extended from the tube and rotated to debride the area concerned. A coupling 5 provides for removal of the specimen, rotation of the brush and independent axial movement of the support 1 and tube 6 relative to each other and the scope 10. One embodiment also provides a liquid supply for use in collecting specimens from dry bodily environs. The invention also includes the method of using such a device in which a brush is rotated to debride area from which a specimen is desired and that specimen is then sucked from the area of the brush for collection and analysis.

15 Claims, 4 Drawing Sheets

CYTOLOGY COLLECTION DEVICE AND METHOD

This invention relates to a cytology collection device and method suitable for collecting cytology samples from both dry and wet bodily environs (e.g. the bladder).

The accuracy of present urine cytology for the detection of malignant transitional cells is said to be anywhere from 15% to 75%. Accuracy depends greatly on the grade and cellularity of the specimen. Low grade tumors are particularly difficult to diagnose by voided cytology. Results with barbotage have been thought to be better. Even for relatively high grade tumors, voided cytology may add little to clinical practice because of the poor cellularity obtained in voided specimens.

It is an object of the present invention to provide, relative to the prior art, a cytology device and method capable of significantly increasing the cellularity of and the quality of cells obtained in liquid specimens (e.g. urine) taken from liquid filled bodily environs.

It is also an object of the present invention to provide such a device and a method in which specimens may be collected from desired selected areas of the bladder.

It is also an object of the present invention to provide a device and method for obtaining biopsy specimen's from normally substantially dry bodily environs (e.g. a lung).

It is also an object of the present invention to provide a device for debriding a desired discrete area of a bodily cavity and for collecting the tissue thereby removed to provide a cytology specimen.

According to the invention there is provided a cytology collection device for the collection of a specimen from a desired area of a bodily environ when the collection device is inserted through an opening to that environ comprising a flexible elongated brush support having proximal and distal ends and being capable of transmitting rotary and longitudinal motion; a debriding brush affixed to the distal end of the brush support; a flexible elongate tube of constant diameter, having proximal and distal ends and, having an internal diameter sufficient to allow the brush to be retracted inside of the distal end thereof, the brush support extending through the tube from the distal end to the proximal end and extending a sufficient distance from the proximal end to allow the brush to be pushed from its retracted position to a position in which it extends from the distal end of the tube while the proximal end of the brush support remains projecting from the proximal end of the tube; a specimen removal and drive coupling attached to the proximal ends of the brush support and tube to allow transfer of a collected specimen from the tube to a specimen removal outlet and to provide a drive coupling for connecting the brush support to a drive means for rotation of the drive support, the coupling being provided with attachment means for removably affixing the device to an inlet to a portal of a scope; the tube being dimensioned to allow passage of a said specimen therethrough past the brush support when the brush is disposed outside the distal end of the tube; wherein the elongate brush support and tube are independently movable longitudinally relative to the attachment means.

Also according to the invention there is provided a cytology collection device in combination with a scope for the collection of a specimen from a desired area of a bodily environ when the combination extends through an opening to that environ, the device comprising a flexible elongate brush support having proximal and distal ends, being capable of transmitting rotary and longitudinal motion and of extending through a portal of the scope; a debriding brush affixed to the distal end of the brush support; and a specimen removal and rive coupling attached to the proximal ends of the brush support to allow transfer of a collected specimen from the portal to a specimen removal outlet and to provide a drive connection for connecting the brush support to a drive coupling for connecting the brush support to a drive means for rotation of the drive support, the coupling being provided with attachment means for and sealingly affixing the device to an inlet to a portal of the scope; wherein the elongate brush support is movable longitudinally relative to the attachment means whereby the brush may be independently longitudinally moved relative to a said portal of the scope into positions in which:

(a) the brush is retracted into the portal, and
(b) the brush extends in its entirety from the portal for the collection of specimen, and the brush.

Also according to the invention there is provided a method of cytology collection, for collecting a specimen, comprising the steps of using a rotating brush to debride a desired area of a bodily environ from which a specimen is to be collected and removing said specimen for analysis, said specimen being removed by suction from the area debrided by the brush; wherein the brush is supported and rotated by an elongate support passing through a tube used for the suction of said specimen from said area, said brush being retracted into said tube prior to reaching said area, and then extended in its entirety from said tube, by means of said support, for rotation to debride said area and to facilitate suction of said specimen through said tube, said support and tube being longitudinally movable independently of one another and of a scope, in a portal through which the brush, support and tube are passed, and with which they are utilized in carrying out the method.

The invention will now be described, by way of example, with reference to the accompanying drawings, in which.

With reference to FIGS. 1-6 of the drawings, a cytology collection device comprises a flexible wire 1, twisted on itself about its axis, extending through an flexible plastic tube 6 from a distal end 2 to a proximal end 4. The wire 1 has an effective outside diameter of no more than about 0.020 inches and the length sufficient to reach the area to be examined (commonly about 16 inches in the case of the bladder). At the distal end 2 of the wire 1 carries a cylindrical debriding brush 3 consisting of radially extending bristles of nylon captured within the twisted wire. Typically the brush may have a diameter of 10 millimeters and a length of 5 millimeters.

The device, at the proximal end 4, terminates in a specimen removal and drive coupling 5 (hereinafter called coupling 5). The coupling 5 is generally cylindrical in shape and includes, in all embodiments illustrated in FIGS. 1 through 6, a connecting passage between the tube 6 and specimen outlet tube 8 for removal of liquid, carrying specimen tissue through the tube 6, by the use of suction. The coupling 5 includes a drive coupling 7 by which the brush may be rotated.

Scope 10 is of a construction known in the prior art and will, therefore, not be described in great detail. The scope 10 illustrated is suitable for insertion through a urethra for the examination of and specimen removal from the bladder. The insertable portion of the scope has a diameter of approximately 0.25 inches and has, extending through it, means for illuminating an area of interest and optical means for observing that area together with a portal, of approximately 0.080 inches diameter. This portal extends from the insertable end of the scope to a connection port 12 which defines a female morse taper adapted to receive a male morse taper for the attachment of an instrument or device extending through the portal of the scope.

Typically the tube 6 has an outside diameter of 0.070 inches and an inside diameter of 0.060 inches whereby it is readily insertable in and through the portal. The scope also includes means operable to bend a flexible portion of the insertable end of the scope in a manner shown in FIG. 2 whereby that end of the scope may be steered and turned to a desired area of the interior surface of the bladder.

When the brush assembly is used in the above mentioned configuration to collect a urine specimen from a bladder, the brush 3 is withdrawn into the tube 6 with the brush compressed into the tube to allow easy passage of the tube through the portal in the scope 10 which has been or is to be passed through the urethra into the bladder. After the placement of the brush, the wire is pushed toward the distal end of the tube assembly allowing the brush to extend beyond the distal end of the tube. The brush 3 is then rotated by means of the drive coupling 7 to cause tissue to be removed from the bladder wall. This removed tissue is deposited in the fluid in the bladder and this fluid is removed from the bladder to be centrifuged for cytological analysis. The use of this device to take cytology samples from specific desired locations of the bladder is facilitated by the mating of this device to an automated device or console which rotates the brush while creating negative pressure within the tube assembly. This negative pressure is applied to the proximal end of the tube assembly to create a negative pressure at the distal end of the assembly immediately adjacent the rotating brush thereby to suck the cells, dislodged by the rotating brush, through the tube and into a collection device. The design features of such collection device are not a part of this invention and are therefor not described in detail herein.

Figure 1:
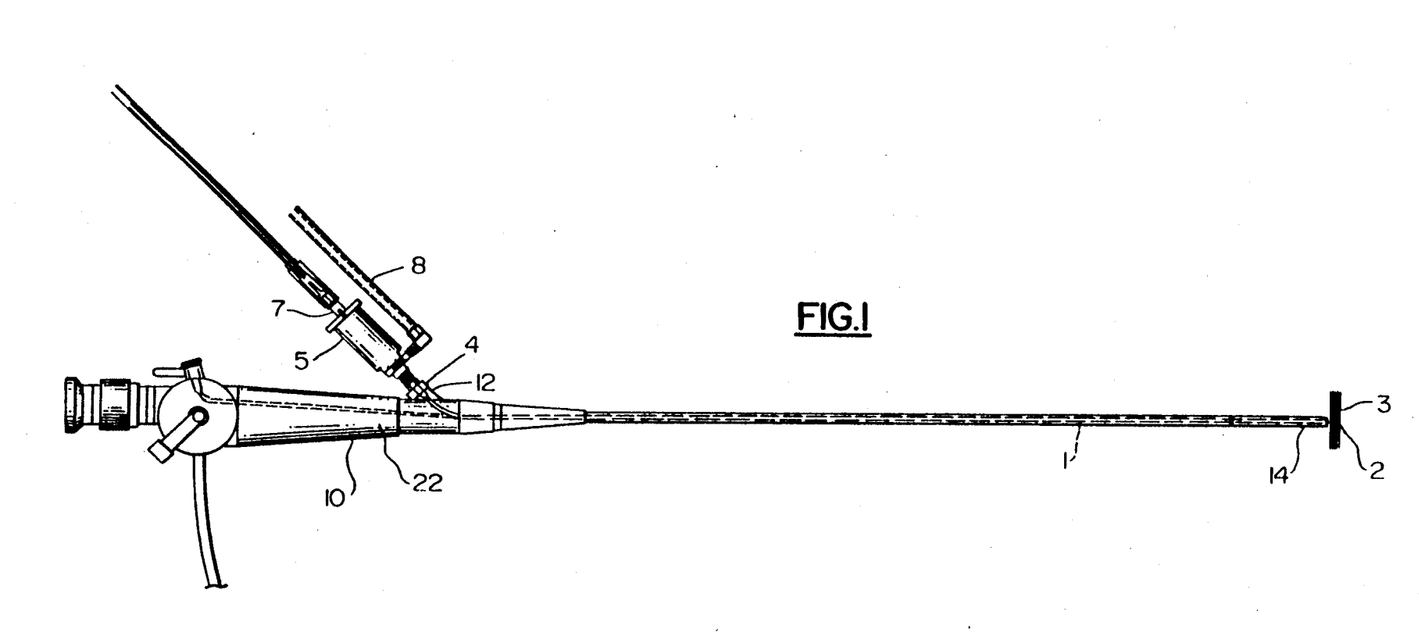
FIG. 1 diagrammatically illustrates a cytology collection device, in combination with a scope, in accordance with the present invention.
Figure 2:
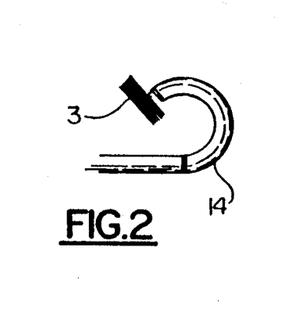
FIG. 2 is a diagrammatic representation of the specimen collection end of the combination illustrated in FIG. 1 with the end of the scope bent into a curved configuration.
Figure 3:
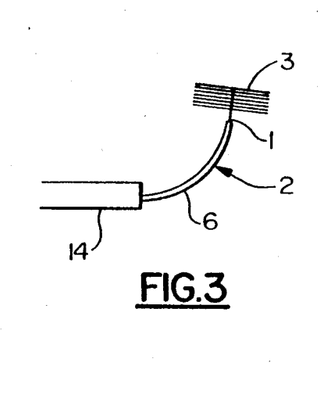
FIG. 3 is a diagrammatic representation of the specimen collection end of the combination illustrated in FIG. 1 with the cytology collection device extending from the end of the scope to form a curved configuration of the brush end of that device.

As shown in FIG. 3, the tube 6 together with the wire 1 may be extended from the insertable end of the scope 10 a sufficient distance to allow the tube 6 and wire 1 to bend upon contact with the wall of the bladder thereby to facilitate the debriding action upon rotation of the brush. The end of the tube 6, at the distal end of the device, is kept close to the brush in order to maximize collection from the selected area and to limit collection from the selected area to tissue removed from the selected area by the debriding action.

The present invention is useful for the collection of cytology specimens from bodily environs which are substantially dry e.g., the lung. To achieve this a supply of liquid is fed through the space between the tube 6 and the portal of scope 10 to the site from which a specimen of tissue is to be removed. The debriding brush is then brought into contact with that site, rotated to remove the tissue by a debriding action in the presence of the supplied liquid. The liquid captures the tissue and is then sucked back through the tube 6 to be removed through the outlet 8.

Figures 4A, 4B:
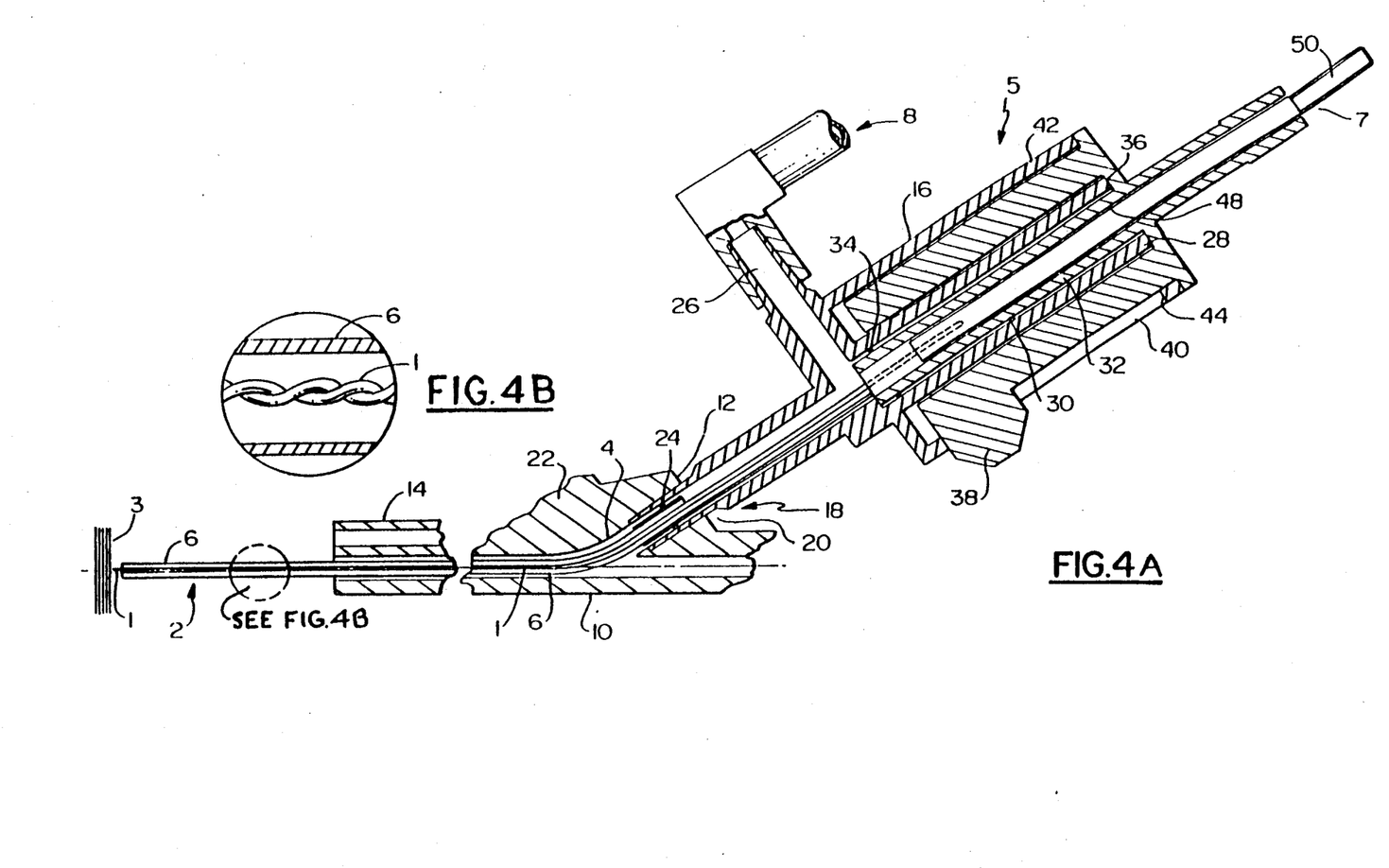
FIGS. 4A and 4B are a fore-shortened longitudinal cross-section of a first embodiment of a cytology collection device, in combination with a scope, of the present invention.

The four exemplary embodiments of the present invention, as illustrated in the drawings, will now be described in greater detail starting with the first embodiment, which is illustrated in FIG. 4. The cytology collection device of FIG. 4, shown in combination with a scope 10, is illustrated with the wire 1 and tube 6 both extending from the insertable end (distal end 14) of the scope 10 in the manner illustrated in FIG. 3 without having been bent into a curve configuration.

The coupling 5 of the first embodiment has a generally cylindrical housing 16 defining at one end 18 a male morse taper shown in engagement with the female morse taper of port 12 of the proximal end 22 of the scope 10. The end 18 defines a central passage through which the proximal end 4 of the device passes into the housing 16 with the tube 6 sealed within that passage by means of an O-ring 24 which permits longitudinal movement of the tube to within the passage while the seal provided by the O-ring 24 is retained, whereby the distal end 2 of the device may be withdrawn into or extended from the portal of the scope is at the distal end 14 thereof. A portion of the sidewall of the tube 6 within the passage is open to the passage to permit the interior of the tube 6 to communicate with an outlet passage 26 extending radially from the device and terminating in a tapered connection for attachment to an outlet tube 8 through which a specimen may be withdrawn. The end 28 of the housing 16, opposite the end 18, defines a cylinder 30 within which is slidably housed a hollow piston member 32 to the hollow interior of which is fixedly attached the end of the tube 6 at the distal end 2 of the device. The piston member is sealed for sliding movement without the cylinder by means of an O-ring 34. The piston member 32 is shown, in FIG. 4, fully inserted into the cylinder 30 to extend the tube 6 the maximum possible distance out from the distal end 14 of the scope 10. A stop 36 on the piston engages the end 28 of the cylindrical housing 16 in this position. The piston member 32 may be removed from the cylinder 30 to an extent limited by a projection 38, connected to the piston member 32, sliding in a slot 40 in an outer cylindrical portion 42 of the cylindrical housing 16. The outward movement of the piston member 32 is limited by engagement of the projection 38 with the end 44 of the slot 40.

The end of the wire 1, at the proximal end 4 of the device, is fixedly attached to the drive coupling which is rotatably and slidably mounted in a central bore 48 of the piston member 32. The drive coupling 7 terminates, externally of coupling 5, in an end 50 having a square cross-section to facilitate connection of a drive device to rotate the wire 1 and, consequently, the brush 3. The drive coupling 7 is axially slidable within the bore 48 to move the wire 1 longitudinally, relative to the tube 6, between the position shown in FIG. 4 in which the brush is extended from the tube 6 at the distal end 2 of the device, to an extent limited by communication of the drive coupling 7 with the end of the tube 6 fixed within the piston member, and a position in which the brush is retracted within the tube 6 at the distal end 2 of the device.

Figure 5:
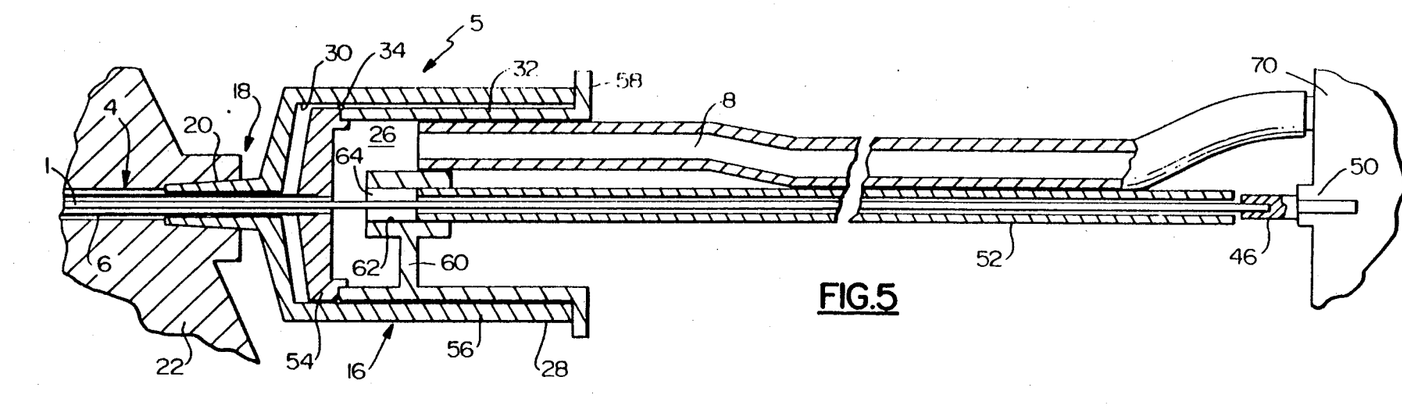
FIG. 5 is a fore-shortened longitudinal cross-section of a second embodiment of a cytology collection device, in combination with a scope, in accordance with the present invention.

Now with reference to FIG. 5 the second embodiment will be described. In this, and the further embodiments, parts which are similar in function will be given reference numerals common to the first embodiment. However, it will appreciated that although these parts share similar functions, details in their design may differ as will be apparent from the associated description and drawings.

Coupling 5 of the second embodiment differs from that of the first embodiment primarily by the extension of wire 1 through the coupling 5 to a remote drive coupling 7 terminating in a square cross-section drive end 50 at a location remote from the coupling 5, the wire 1 extending to that location through a flexible outer support tube 52 which permits axial and rotary motion of the wire 1 relative thereto. In addition, the outlet 8 comprises a tube extending substantially parallel to the extension of the wire 1 to the drive coupling 7 whereby the connection of this tube and the drive coupling 7 to a console 70 which provides suction for the outlet and a rotary drive for wire 1 is facilitated. Of course the wire 1 could be terminated in the coupling 5 at a connector attached to a wire extending through the tube 52 to the console 70.

In the second embodiment the cylindrical housing 16 defines a cylinder 30 of somewhat larger diameter than that of the first embodiment. Again, the piston member 32 engaged within the cylinder 30 for axial movement therein in a sealed manner ensured by the presence of O-ring 34 engaged in a groove in the piston number 32 for sealing engagement with the cylinder 30. The piston member 32 is an assembly comprising a piston head 54 which is fixedly attached to a cylindrical portion 56 (corresponding in essence to a piston skirt) terminating at its end remote from the piston head 54 in an outwardly extending annular flange 58 which serves to provide a grip for sliding the piston in the cylinder and a stop with respect to the maximum inward movement of the piston in the cylinder, namely abutment of the flange 58 with the outer end 28 of the cylindrical housing 16 as shown in FIG. 5. Tube 6 is fixedly attach in a bore, centrally disposed axially in the piston head 54, that provides clearance for flow of a specimen from the tube 6 into an outlet passage 26.

In view of the sealed attachment of the tube 6 to the piston head, no O-ring 24 is required in this embodiment. In fact, the passage in the end 18 can be provided with an annular clearance from tube 6. The outlet passage 26 communicates with the outlet 8 which is a tube fixedly sealed in an opening of a web which serves as part of the structure defining the passage 26 and which extends transversely across a bore defined by the pistons skirt 56. That web 60 also defines a central bore 62 through which the wire 1 extends from the proximal end 4 of the device to enter and pass through the support tube 52 which in turn is fixedly attached inside the bore 62.

In this second embodiment coupling 5 is shown in a position in which the tube and brush are fully extended from the distal end of the scope in a similar manner to the arrangement shown in FIG. 4. In this second embodiment, tube 6 is moved by moving the piston number 32 axially in the cylinder 30 while the wire 1 is moved axially by movement of the drive coupling 7 within the limits imposed by the termination of the support tube 52 adjacent the drive coupling 7. The wire is sealed in the bore 62 by a cylindrical resilient seal 64 which permits both the axial and rotary motion of the wire relative to the seal.

In addition, although not shown with respect to the second embodiment, stop means is provided to prevent the piston member 32 from being completely removed from the cylinder 30. Such stop means may be similar to that provided and described with reference to the first embodiment.

Figure 6:
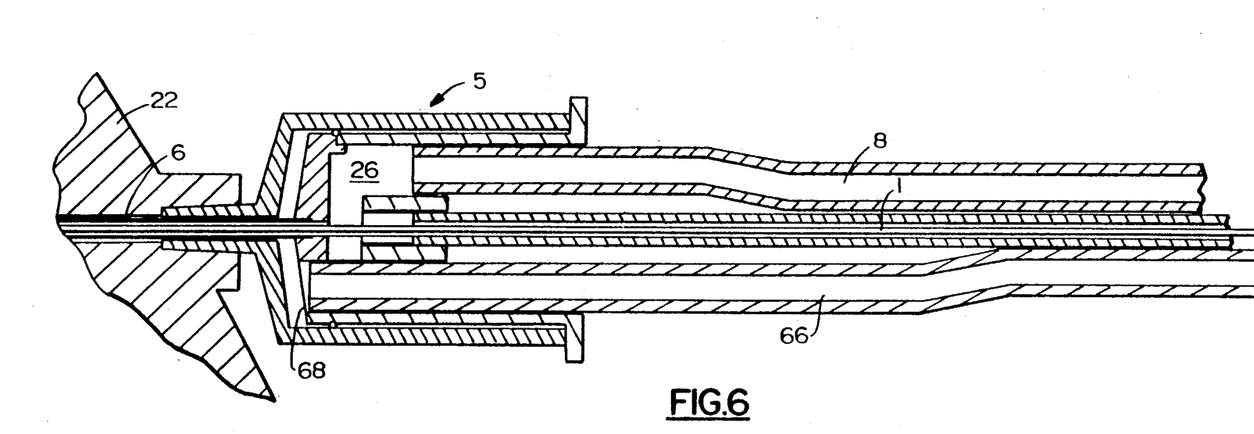
FIG. 6 is a fore-shortened longitudinal cross-section of a third embodiment of a cytology collection device, in combination with a scope, in accordance with the present invention.

The third embodiment will now be described with reference to FIG. 6. The first and second embodiment are concerned with a cytology collection device primarily for use in wet environments, for example for collecting specimens from the inside of a bladder. The third embodiment, however, is suitable for the collection of tissue specimens from relatively dry cavities, for example lungs. The cytology collection device of this third embodiment differs from the second embodiment in two respects. The first of these is the provision of a liquid supply tube 66 which extends through the web 60, in sealed engagement therewith to be fixedly attached in a sealed manner in an opening 68 in the piston head 54 for the supply of liquid to the space between the piston head 54 and the end of the cylindrical housing 16. The second difference is the provision of sufficient annular clearance between the passage extending through the male morse taper 20 and the tube 6 for liquid supplied through the tube 66 to pass into the annular space between the tube 6 and the portal for passage to the distal end 14 of the scope 10 to supply the area to be debrided and to capture the debrided tissue. The tissue carrying liquid specimen is then carried back through the tube 6, under the suction previously discussed, to the outlet tube 8. In this connection, it should be noted that the portal generally has a diameter (or an average diameter) which provides an average radial clearance between the tube 6 and the portal of about 0.005 inches. As with the second embodiment the O-ring 24 may be omitted in the third embodiment.

Figure 7:
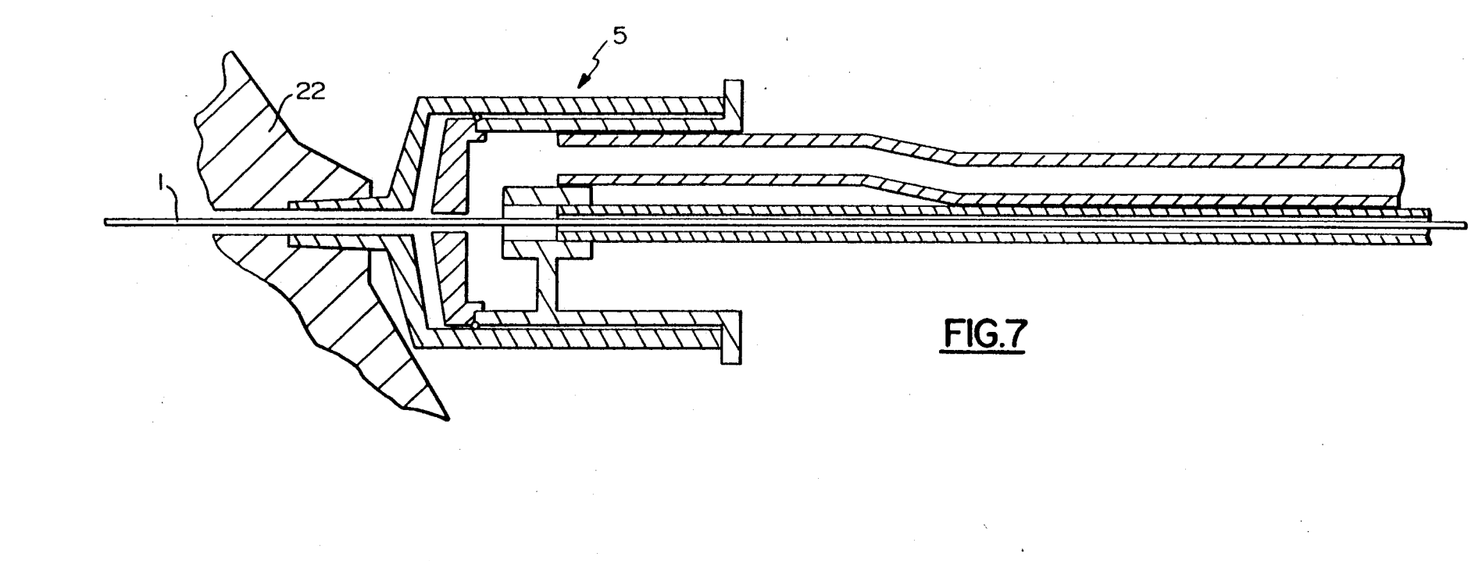
FIG. 7 is a fore-shortened longitudinal cross-section of a fourth embodiment of a cytology collection device, in combination with a scope, in accordance with the present invention.

The fourth embodiment is illustrated in FIG. 7 and differs from the second embodiment by the omission of tube 6 from the cytology collection device. In this embodiment the brush 3 prior to use is simply recessed in the distal end 14 of the scope 10 from which it may be extended to provide a desired specimen to be sucked back through the annular space between the wire 1 and the portal, past the sealing engagement of the male and female morse taper and through the passage 26 to the outlet tube 8.

It will be appreciated that while the four embodiments described above have been described individually, various features could be combined to produce embodiments the construction of which would be apparent to a man skilled in the art. For example, a dry coupling arrangement of the first embodiment could be replaced with the drive arrangement discussed with respect to the second embodiment to facilitate the connection of the cytology collection device of the first embodiment to the control and specimen recovery console 70.

Figure 8:
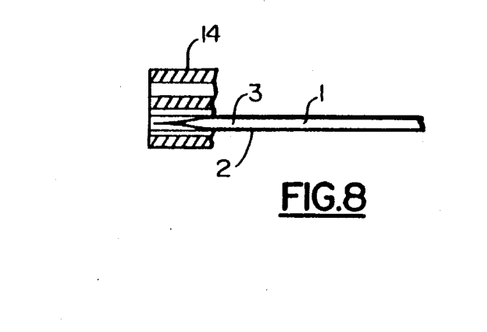
FIG. 8 illustrates the insertable end of a scope with the cytology collection device withdrawn into a portal thereof.

FIG. 8 illustrates the distal end 14 of the scope 10 with the brush 3 withdrawn in collapsed condition into the end of the tube 6 at the distal end of the cytology collection device.

Figure 9:
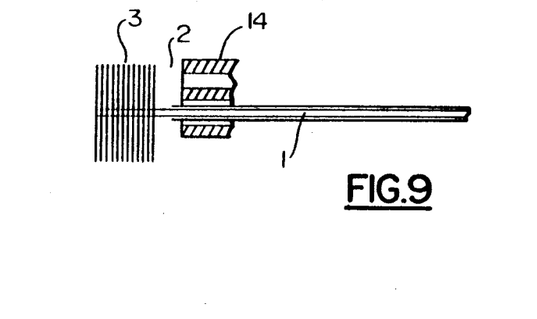
FIG. 9 illustrates the insertable end of a scope with the cytology collection device extending just outside of the portal through which it extends.

FIG. 9 illustrates a condition in which the tube 6 projects slightly from the portal at the distal end 14 of the scope 10 a situation in which the brush has been extended from the end of the tube 6 in order that it may expand to its debriding condition in which it is a cylindrical brush consisting of a plurality of radial nylon bristles.

I claim:

1. A cytology collection device for the collection of a specimen from a desired area of a bodily environ when the collection device is inserted through an opening to that environ comprising:
   a flexible elongate brush support having proximal and distal ends and being capable of transmitting rotary and longitudinal motion;
   a debriding brush affixed to the distal end of the brush support;
   a flexible elongate tube of constant diameter, having proximal and distal ends and, having an internal diameter sufficient to allow the brush to be retracted inside of the distal end thereof, the brush support extending through the tube from the distal end to the proximal end and extending a sufficient distance from the proximal end to allow the brush to be pushed from its retracted position to a position in which it extends from the distal end of the tube while the proximal end of the brush support remains projecting from the proximal end of the tube;
   the tube being dimensioned to allow passage of a said specimen therethrough past the brush support when the brush is disposed outside the distal end of the tube;
   a specimen removal and drive coupling attached to the proximal ends of the brush support and tube to allow transfer of a collected specimen from the tube to a specimen removal outlet and to provide a drive connection for connecting the brush support to a drive means for rotation of the drive support, the coupling being provided with attachment means for removably affixing the device to an inlet to a portal of a scope;
   the coupling having control means whereby the elongate brush support and tube are independently movable longitudinally relative to the attachment means.

2. A cytology collection device according to claim 1 wherein the attachment means defines an opening through which the tube passes to a longitudinally movable means, to which the tube is attached, for providing said relative movement thereof, the tube being open within the coupling to provide for transfer of a collected specimen only to the specimen removal outlet of the coupling.

3. A cytology collection device according to claim 2 wherein said longitudinally movable means comprises a piston, to which the tube is attached, reciprocable in sealed manner within a cylinder defined by the coupling, the elongate brush support passing through the piston and a seal, which permits the rotary movement and the longitudinal relative movement of that support, to a drive connector to which that support is affixed to provide for said movements thereof.

4. A cytology collection device according to claim 3 wherein the tube is sealingly slidable in the opening of the attachment means, the seal is in the piston, the proximal end of the tube is closed and the tube has a transverse opening to provide for said transfer.

5. A cytology collection device according to claim 3 wherein the seal is in the piston and the proximal end of the tube is open to a chamber defined within the piston to provide for said transfer to the specimen removal outlet, which is also defined by the piston.

6. A cytology collection device according to claim 5 wherein an annular clearance is provided between the tube and the opening in the attachment means and a fluid supply inlet of the coupling connects with the annular clearance by way of a space between the piston and a head, of the cylinder, connected to the attachment means, whereby fluid can be supplied between the tube and a portal of a scope, through which the tube has been passed, to the desired area.

7. A cytology collection device according to claim 1 in combination with a scope through a portal of which the device extends, the tube and brush being independently movably longitudinally relative to the portal by said control means into positions in which:
   a) both the tube and the brush are retracted into the portal with the brush retracted into the tube,
   b) the brush extends in its entirety from the portal for the collection of a specimen, and
   c) the brush and the tube extend from the portal with the brush entirely outside of the distal end of the tube for the collection of the specimen with the tube in close proximity thereto for receipt of the collected specimen.

8. A cytology collection device according to claim 1 in combination with a scope having a portal through which the device extends with the attachment means removably affixed to a cooperating attachment means of the scope.

9. A cytology collection device according to claim 8 wherein the attachment means defines an opening through which the tube passes to a longitudinally movable means, to which the tube is attached, for providing said relative movement thereof, the tube being open within the coupling to provide for transfer of a collected specimen only to the specimen removal outlet of the coupling.

10. A cytology collection device according to claim 9 wherein said longitudinally movable means comprises a piston, to which the tube is attached, reciprocable in sealed manner within a cylinder defined by the coupling, the elongate brush support passing through the piston and a seal, which permits the rotary movement and the longitudinal relative movement of that support, to a drive connector to which that support is affixed to provide for said movements thereof.

11. A cytology collection device according to claim 10 wherein the tube is sealingly slidable in the opening of the attachment means, the seal is in the piston, the proximal end of the tube is closed and the tube has a transverse opening to provide for said transfer.

12. A cytology collection device according to claim 10 wherein the seal is in the piston and the proximal end of the tube is open to a chamber defined within the piston to provide for said transfer to the specimen removal outlet, which is also defined by the piston.

13. A cytology collection device according to claim 12 wherein an annular clearance is provided between the tube and the opening in the attachment means and a fluid supply inlet of the coupling connects with the annular clearance by way of a space between the piston and a head, of the cylinder, connected to the attachment means, whereby fluid can be supplied between the tube and the portal of the scope, through which the tube has been passed, to the desired area.

14. A method of cytology collection, for collecting a specimen, utilizing a cytology collection device comprising:
- a flexible elongate brush support having proximal and distal ends and being capable of transmitting rotary and longitudinal motion;
- a debriding brush affixed to the distal end of the brush support;
- a flexible elongate tube of constant diameter, having proximal and distal ends and, having an internal diameter sufficient to allow the brush to be retracted inside of the distal end thereof, the brush support extending through the tube from the distal end to the proximal end and extending a sufficient distance from the proximal end to allow the brush to be pushed from its retracted position to a position in which it extends from the distal end of the tube while the proximal end of the brush support remains projecting from the proximal end of the tube;
- the tube being dimensioned to allow passage of a said specimen therethrough past the brush support when the brush is disposed outside the distal end of the tube;
- a specimen removal and drive coupling attached to the proximal ends of the brush support and tube to allow transfer of a collected specimen from the tube to an outlet and to provide a drive connection for connecting the brush support to a drive means for rotation of the drive support, the coupling being provided with attachment means for removably affixing the device to an inlet to a portal of a scope;
- the coupling having control means whereby the elongate brush support and tube are independently movable longitudinally relative to the attachment means;
- comprising the steps rotation the brush to debride a desired area of a bodily environ from which a specimen is to be collected and removing said specimen for analysis, said specimen being removed by suction from the area debrided by the brush; wherein the brush is supported the rotated by an elongated support passing through the tube used for the suction of said specimen from said area, said brush being retracted into said tube prior to reaching said area, and then extended in its entirety from said tube, by means of said support, for rotation to debride said area and to facilitate suction of said specimen through said tube, said support and tube being longitudinally moveable independently of one another and of a scope, in a portal through which the brush, support and tube are passed, and with which they are utilized in carrying out the method.

15. A method according to claim 14 including the step of supplying liquid through a space between the tube and the portal to the desired area to receive tissue produced by the debriding action of the brush to form the specimen.

* * * * *

UNITED STATES PATENT AND TRADEMARK OFFICE
CERTIFICATE OF CORRECTION

PATENT NO. : 5,217,023

DATED : June 8, 1993

INVENTOR(S) : Robert S. LANGDON

It is certified that error appears in the above-identified patent and that said Letters Patent is hereby corrected as shown below:

Column 7, line 60 replace "coupling" with --device--.

Column 10, line 12 replace "coupling" with --device--.

Signed and Sealed this

Ninth Day of May, 1995

Attest:

BRUCE LEHMAN

*Attesting Officer*  *Commissioner of Patents and Trademarks*